United States Patent [19]

Wang et al.

[11] Patent Number: 5,066,426
[45] Date of Patent: Nov. 19, 1991

[54] FLUORESCENCE POLARIZATION IMMUNOASSAY UTILIZING SUBSTITUTED CARBOXYFLUORESCEINS

[75] Inventors: Chao-Huei J. Wang, Gurnee; Stephen D. Stroupe, Libertyville; Michael E. Jolley, Round Lake, all of Ill.

[73] Assignee: Abbott Laboratories, North Chicago, Ill.

[21] Appl. No.: 644,172

[22] Filed: Aug. 23, 1984

Related U.S. Application Data

[60] Continuation of Ser. No. 443,401, Nov. 22, 1982, abandoned, which is a division of Ser. No. 329,974, Dec. 11, 1981, abandoned, which is a continuation-in-part of Ser. No. 235,259, Feb. 17, 1981, abandoned.

[51] Int. Cl.$^5$ .......................... C07J 21/00; C07J 19/00
[52] U.S. Cl. ..................................... 540/106; 544/311; 544/350; 548/487; 540/114
[58] Field of Search .................................... 260/239.57

[56] References Cited

U.S. PATENT DOCUMENTS

| | | | |
|---|---|---|---|
| 4,060,607 | 11/1977 | Jarreau et al. | 260/239.57 |
| 4,082,747 | 4/1978 | Chen | 260/239.57 |
| 4,217,280 | 8/1980 | Jarreau et al. | 260/239.57 |

*Primary Examiner*—Elbert L. Roberts
*Attorney, Agent, or Firm*—James L. Wilcox; Dennis K. Shelton

[57] ABSTRACT

This disclosure relates to a method and reagents for determining ligands in biological fluids such as serum, plasma, spinal fluid, amnionic fluid and urine. In particular, this disclosure relates to a fluorescence polarization immunoassay procedure and to a novel class of tracer compounds employed as reagents in such procedures. The procedure disclosed combines the specificity of an immunoassay with the speed and convenience of fluorescence polarization techniques to provide a means for determining the amount of a specific ligand present in a sample.

1 Claim, No Drawings

FLUORESCENCE POLARIZATION IMMUNOASSAY UTILIZING SUBSTITUTED CARBOXYFLUORESCEINS

This is a continuation of application Ser. No. 443,401, filed Nov. 22, 1982, now abandoned, which is a divisional of Ser. No. 329,974, filed Dec. 11, 1981, now abandoned, which is a continuation-in-part of abandoned Ser. No. 235,259, Feb. 17, 1981.

BACKGROUND OF THE INVENTION

The present invention relates to a method and reagents for determining ligands in biological fluids such as serum, plasma, spinal fluid, amnionic fluid and urine. In particular, the present invention relates to a fluorescence polarization immunoassay procedure and to tracers employed as reagents in such procedures. The fluorescence polarization immunoassay procedure of the present invention combines the specificity of an immunoassay with the speed and convenience of fluorescence polarization techniques to provide a means for determining the amount of a specific ligand present in a sample.

Competitive binding immunoassays for measuring ligands are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitively measured and is inversely proportional to the quantity of ligand in the test sample.

In general, fluorescence polarization techniques are based on the principle that a fluorescent labeled compound when excited by linearly polarized light will emit fluorescence having a degree of polarization inversely related to its rate of rotation. Therefore, when a molecule such as a tracer antibody conjugate having a fluorescent label is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescence polarization provides a quantitive means for measuring the amount of tracer-antibody conjugate produced in a competitive binding immunoassay. Various fluorescent labeled compounds are known in the art. U.S. Pat. No. 3,998,943 describes the preparation of a fluorescently labeled insulin derivative using fluorescein isothiocyanate (FITC) as the fluorescent label and a fluorescently labeled morphine derivative using -aminofluorescein hydrochloride as the fluorescent label. Carboxyfluorescein has also been used for analytical determinations. R. F. Chen, Anal. Lett., 10, 787 (1977) describes the use of carboxyfluorescein to indicate the activity of phospholipase. However, carboxyfluorescein is not conjugated according to the present invention. It is encapsulated in lecithin liposomes, and it will fluoresce only when released by the hydrolysis of lecithin.

SUMMARY OF THE INVENTION

The present invention encompasses a method for determining ligands in a sample comprising intermixing with said sample a biologically acceptable salt of a tracer of the formula

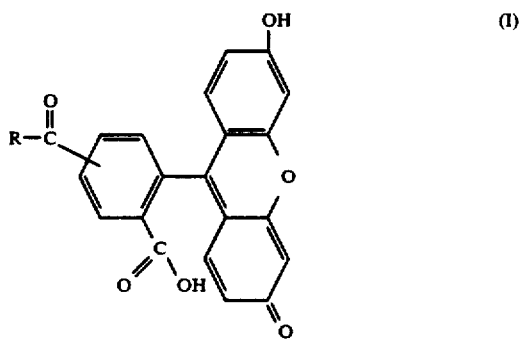

wherein R is a ligand-analog having a single reactive primary or secondary amino group which is attached to the carbonyl carbon of the carboxyfluorescein wherein said ligand-analog has at least one common epitope with said ligand so as to be specifically reconizable by a common antibody;

and an antibody capable of specifically recognizing said ligand and said tracer; and then determining the amount of tracer antibody conjugate by fluorescence polarization techniques as a measure of the concentration of said ligand in the sample.

The invention further relates to certain novel tracers and biologically acceptable salts thereof, which are useful in reagents in the above-described method. The methods and tracers of the present invention are particularly useful in quantitatively monitoring therapeutic drug concentrations in serum and plasma.

DETAILED DESCRIPTION OF THE INVENTION

The term "ligand" as used herein refers to a molecule, in particular a low molecular weight hapten having a single reactive amino group, to which a receptor, normally an antibody, can be obtained or formed. Such haptens are protein-free bodies, generally of low molecular weight that do not induce antibody formation when injected into an animal, but are reactive to antibodies. Antibodies to hapten are generally raised by first conjugating the haptens to a protein and injecting the conjugate product into an animal. The resulting antibodies are isolated by conventional antibody isolation techniques.

Ligands determinable by the method of the present invention vary over a wide molecular weight range. Although high molecular weight ligands may be determined, for best results, it is generally preferable to employ the methods of the present invention to determine ligands of low molecular weight, generally in a range of 50 to 4000. It is more preferred to determine ligands having a molecular weight in a range of 100 to 2000.

The novel tracers of the present invention include compounds of formula (I) wherein the ligand-analog represented by R include radicals having a molecular weight within a range of 50 to 4000. The preferred novel tracers include compounds of formula (I) wherein the ligand-analogs represented by R include radicals having a molecular weight within a range of 100 to 2000.

Representative of ligands having a single reactive amino group determinable by the methods of the present invention include steriods such as esterone, estradoil, cortisol, testoestrone, progesterone, chenodeoxycholic acid, digoxin, cholic acid, digitoxin, deoxycholic acid, lithocholic acids and the ester and amide derivatives thereof; vitamins such as B-12, folic acid; thyroxine, triiodothyronine, histamine, serotonin, prostaglandins such as PGE, PGF, PGA; antiasthmatic drugs such as theophylline, antineoplastic drugs such as doxorubicin and methotrexate antiarrhythmic drugs such as disopyramide, lidocaine, procainamide, propranolol, quinidine, N-acetyl-procainamide; anticonvulsant drugs such as phenobarbital, phenytoin, primidone, valproic acid, carbamazepine and ethosuximide; antibiotics such as penicillins, cephalosporins and vancomycin; antiarthritic drugs such as salicylate; antidepressant drugs including tricyclics such as nortriptyline, amitriptyline, imipramine and desipramine; and the like as well as the metabolites thereof. Additional ligands that may be determined by the methods of the present invention include drugs of abuse such as morphine, heroin, hydromorphone, oxymorphone, metapon, codeine, hydrocodone, dihydrocodeine, dihydrohydroxy, codeinone, pholcodine, dextromethorphan, phenazocine and deonin and their metabolites.

The tracers of the present invention generally exist in an equilibrium between their acid and ionized states, and in the ionized state are effective in the method of the present invention. Therefore, the present invention comprises the tracers in either the acid or ionized state and for convenience, the tracers of the present invention are structurally represented herein in their acid form. When the tracers of the present invention are present in their ionized state, the tracers exist in the form of biologically acceptable salts. As used herein, the term "biologically acceptable salts" refers to salts such as sodium, potassium, ammonium and the like which will enable the tracers of the present invention to exist in their ionized state when employed in the method of the present invention. Generally, the tracers of the present invention exist in solution as salts, the specific salt results from the buffer employed, i.e., in the presence of a sodium phosphate buffer, the tracers of the present invention will generally exist in their ionized state as a sodium salt.

The tracers of the present invention comprise a ligand-analog represented by R linked to a carboxyfluorescein moiety of the formula:

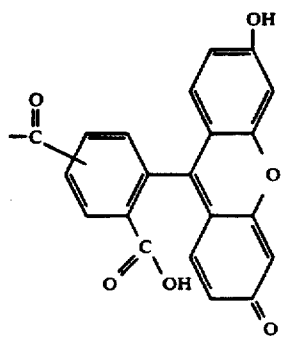

(II)

The term ligand-analog as used herein refers to a mono or polyvalent radical a substantial proportion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand analog will have the same or substantially the same structure and charge distribution (spatial and polar organization) as the ligand of interest for a significant portion of the molecular surface. Since frequently, the linking site for a hapten will be same in preparing the antigen for production of antibodies as used for linking to the ligand, the same portion of the ligand analog which provides the template for the antibody will be exposed by the ligand analog in the tracer.

In general, the class of ligand analogs represented by R are derived from the corresponding ligand by removal of a reactive hydrogen atom, i.e., a hydrogen atom bonded to a reactive amine (primary or secondary) or by the formation of an amino derivative of the ligand wherein an imino group $$\begin{array}{c} H \\ | \\ -N- \end{array}$$

replaces one or more atoms originally present in the ligand, at the site of binding to the carboxyfluorescein moiety. Illustrative of ligands which upon the removal of a reactive hydrogen may form ligand-analogs represented by R include for example, procainamide, thyroxine and quinidine. Illustrative of ligands whose amino derivatives are useful as ligand-analog include theophylline, valproic acid, phenobarbital, phenytoin, primidone, disopyramide, digoxin, chloramphenicol, salicylate, acetaminophen, carbamazepine, desipramine and nortriptyline. In addition, a ligand may be structurally modified by the addition or deletion of one or more functional groups to form a ligand-analog, while retaining the necessary epitope sites for binding to an antibody. However, such modified ligand-analogs are bonded to the carboxyfluorescein moiety through an imino group.

The tracers of the present invention are generally prepared in accordance with known techniques. For example, a compound of the formula:

R—X         (III)

wherein R is above-defined and X is a reactive hydrogen; is treated with a compound of the formula:

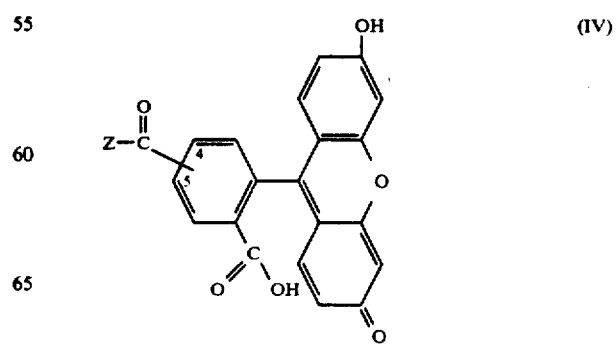

(IV)

wherein R is hydroxy or an active ester, and wherein the carboxy group is preferably bonded to the 4 or 5 position of the benzoic acid ring; in the presence of an inert solvent to yield a compound of formula (I).

As used herein, the term "active ester" refers to a moiety which is readily "removed" from the carboxy carbon in the presence of a coupling agent. Such "active esters" of carboxyfluorescein are readily ascertained by one of ordinary skill in the art and are prepared from the reaction of carboxyfluorescein with a compound such as N-hydroxysuccinimide, 1-hydroxybenzotriazole.hydrate or p-nitrophenol in the presence of a coupling agent, such as dicyclohexylcarbodiimide and a solvent. The active esters of carboxyfluorescein thus produced are subsequently reacted with a compound of formula (III) to yield a tracer of formula (I).

If the compound of formula (III) is water soluble, the reaction mechanism proceeds by directly reacting carboxyfluorescein with a compound of formula (III) in aqueous solution in the presence of a water soluble carbodiimide, such as 1-ethyl-3-(3'-dimethylaminopropyl)-carbodiimide hydrochloride, as a coupling agent.

The temperature at which the process for preparing the tracers of this invention proceeds is not critical. The temperature should be one which is sufficient so as to initiate and maintain the reaction. Generally, for convenience and economy, room temperature is sufficient. In preparing the tracers of the present invention, the ratio of reactants is not narrowly critical. For each mole of a compound of formula II), one should employ one mole of a compound of formula (III) to obtain a reasonable yield. It is preferred to employ an excess of compound of formula (III) for ease of reaction and recovery of the reaction products.

For ease in handling and recovery of product, the process for preparing the tracers of the present invention is conducted in the presence of an inert solvent. Suitable inert solvents include those solvents which do not react with the starting materials and are sufficient to dissolve the starting materials, and include for example water (if the compound of formula (III) is water soluble), dimethylformamide, dimethylsulfoxide and the like. If the compound of formula (III) is a reactive amine salt, a suitable base is added to the reaction mixture to form the free base of the reactive amine. Suitable bases include for example, triethylamine. The reaction products of formula (I) are generally purified using either thin-layer or column chromatography prior to application in the methods of the present invention.

In accordance with the method of the present invention, a sample containing the ligand to be determined is intermixed with a biologically acceptable salt of a tracer of formula (I) and an antibody specific for the ligand and tracer. The ligand present in the sample and the tracer compete for limiting antibody sites resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, upon exciting the mixture with polarized light and measuring the polarization of the fluorescence emitted by a tracer and a tracer-antibody complex, one is able to quantitatively determine the amount of ligand in the sample.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertical component of the emitted light, the polarization of fluorescence in the reaction mix may be accurately determined. The precise relationship between polarization and concentration of the ligand to be determined is established by measuring the polarization values of calibrators with known concentrations. The concentration of the ligand can be extrapolated from a standard curve prepared in this manner.

The pH at which the method of the present invention is practiced must be sufficient to allow the tracers of formula (I) to exist in their ionized state. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about 0° to 50° C., more usually from about 15° to 40° C.

The concentration of ligand which may be assayed will generally vary from about $10^{-2}$ to $10^{-13}$M, more usually from about $10^{-4}$ to $10^{-10}$M. Higher concentrations of ligand may be assayed upon dilution of the original sample.

In addition to the concentration range of ligand of interest, considerations such as whether the assay is qualitative, semiquantitative or quantitative, the equipment employed, and the characteristics of the tracer and antibody will normally determine the concentration of the tracer and antibody to be employed. While the concentration of ligand in the sample will determine the range of concentration of the other reagents, i.e., tracer and antibody, normally to optimize the sensitivity of the assay, individual reagent concentrations will be determined empirically. Concentrations of the tracer and antibody are readily assertained by one of ordinary skill in the art.

As previously mentioned the preferred tracers of the present invention are prepared from 5-carboxyfluorescein or 4-carboxyfluorescein or mixtures thereof and are represented by the formulas:

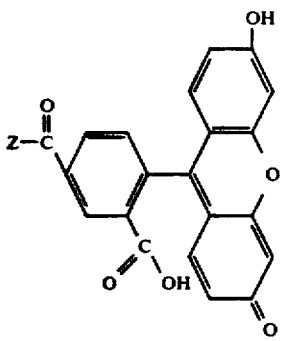

(V)

or

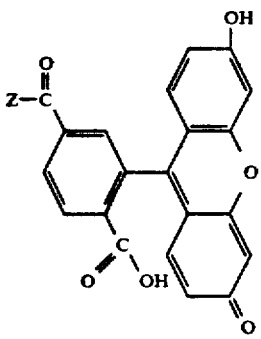

(VI)

The following illustrative, nonlimiting examples will serve to further demonstrate to those skilled in the art the manner in which specific tracers within the scope of the is invention may be prepared. The symbol [CF] appearing in the structural formulas illustrating the compounds prepared in the following examples, represents a moiety of the formula:

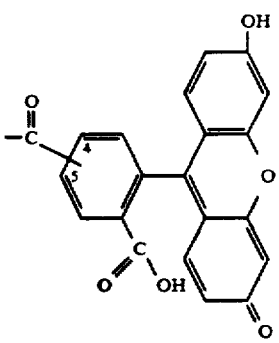

(VII)

wherein the carbonyl carbon is attached to position in the above formula in view of the fact that a mixture of 4- and 5-carboxyfluorescein is employed as starting material.

EXAMPLE I

Meta- or para- aminophenobarbital (5 mg) and carboxyfluorescein (5 mg) were dissolved in 0.5 ml of pyridine. To the mixture was added N,N'-dichohexylcarbodiimide (15 mg). The reaction proceeded for two hours at room temperature, after which time the reaction product was purified twice employing silica gel thin-layer chromatography using a chloroform:methanol (2:1) mixture as developing solvent to yield an aminophenobarbital-carboxyfluorescein conjugate of the formula:

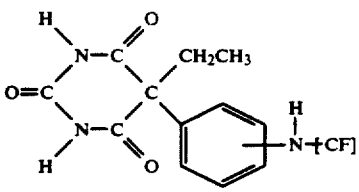

EXAMPLE II

A solution containing sodium hydroxide (1.0 g), phenytoin (2.5 g) and 2-bromomethylamine hydrobromide (2.0 g) in 100 ml of 100% ethanol was refluxed for two hours and then evaporated to dryness under reduced pressure. The residue was suspended in 50 ml of water and the pH was adjusted to pH 11 by the addition of 6N sodium hydroxide to dissolve any unreacted phenytoin. The remaining precipitate, 2-$\beta$-aminoethylphenytoin, was filtered, rinsed thoroughly with water and dried.

An active ester of carboxyfluorescein was prepared by dissolving N-hydroxysuccinimide (5 mg), carboxyfluorescein (7.5 mg) and N,N'-dicyclohexylcarbodiimide (20 mg) in 0.5 ml of pyridine. The reaction was allowed to proceed for two hours at room temperature after which time 2-$\beta$-aminoethylphenytoin (10 mg) was dissolved in the reaction mixture. The resulting mixture was allowed to react overnight in the dark at room temperature and the reaction product was purified twice employing silica gel thin-layer chromatography using a chloroform:methanol (3:1) mixture as developing solvent to yield a 2-$\beta$-aminoethylphenytoin-carboxyfluorescein conjugate of the formula:

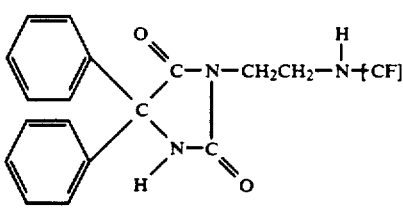

EXAMPLE III

A solution containing 2-carboxymethylphenytoin (620 mg), N-hydroxysuccinimide (248 mg) and N,N'-dicyclohexylcarbodiimide (453 mg) in 6 ml of dry dimethylsulfoxide was allowed to stand at room temperature overnight. The mixture was filtered and 0.7 ml of 95% hydrozine was added to 4.5 ml of the filtrate. After four hours at room temperature, 40 ml of water and 0.5 ml of 10% sodium hydroxide were added to the reaction mixture. The precipitate, 2-carboxymethylphenytoin hydrazide, was filtered, rinsed with water, dried and used without further purification.

N,N'-dicyclohexylcarbodiimide (15 mg) was added to a solution of 2-carboxymethylphenytoin hydrazide (5 mg) and carboxyfluorescein (5 mg) in 0.5 ml of pyridine. The reaction was allowed to proceed for two hours at room temperature, and the reaction product was then purified twice employing silica gel thin-layer chromatography using a chloroform:acetone (1:1) mixture as developing solvent to yield a 2-carboxymethylphenytoin hydrazide-carboxyfluorescein conjugate of the formula:

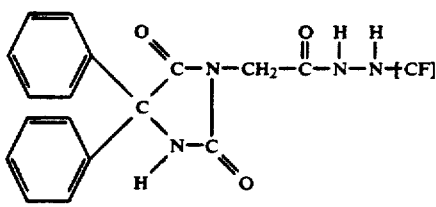

EXAMPLE IV

N,N'-dicyclohexylcarbodiimide (15 mg) was added to a solution of 8-β-aminoethyltheophylline (5 mg) and carboxyfluorescein (5 mg) in 0.5 ml of pyridine. The reaction was allowed to proceed for two hours at room temperature and the reaction product was purified twice employing silica gel thin-layer chromatography using a thin chloroform:methanol (2:1) mixture as developing solvent to yield an 8-β-amino ethyltheophylline-carboxyfluorescein conjugate of the formula:

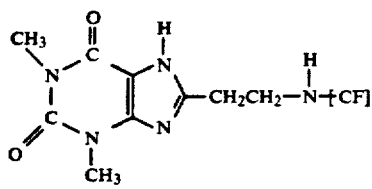

EXAMPLE V

The procedure of Example IV was employed utilizing β-aminomethyltheophylline in lieu of 8-β-aminoethylthoephylline to yield an 8-aminomethylthoephylline-carboxyfluorescein conjugate of the formula:

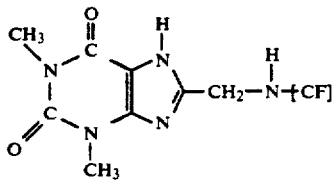

EXAMPLE VI

δ-Valerolactam (7.5 g) was dissolved in 60 ml of dry tetrahydrofuran, under a dry nitrogen atmosphere and n-butyllithium (1.6 M, 90 ml) in hexane were added dropwise to the reaction flask and chilled in a dry ice-acetone bath. Upon completion of the addition of n-butyllithium, the . reaction mixture was stirred at room temperature for one hour, reflexed for thirty minutes, and cooled to room temperature under dry nitorgen atmosphere. 1-Bromoethane (8.0 g) was slowly added to the reaction flask while the flask was chilled in an ice bath. The resulting mixture was then stirred for sixteen hours at room temperature after which time 100 ml of water was slowly added. The resulting mixture was stirred at room temperature for thirty minutes and the organic layer separated. The aqueous layer was extracted with 50 ml of diethyl ether and the organic layers were combined and dried over sodium sulfate. The solvent was evaporated to give a dark oil, which crystallized on standing. The crystalline residue was recrystallized from petroleum ether to yield 3.8 g of a residue. The residue (2.8 g) was refluxed in 25 ml of 6N hydrochlorid acid for six hours. The water was evaporated from the mixture to yield a dark, thick oil—2-ethyl-5-aminopentanoic acid/—which was used without further purification.

An active ester of carboxyfluorescein was prepared by dissolving N-hydroxysuccinimide (5 mg), carboxyfluorescein (7.5 mg) and N,N'-dicyclohexylcarbodiimide (20 mg) in 0.5 ml of pyridine. The reaction was allowed to proceed for two hours at room temperature, after which time 2-ethyl-5-aminopentanoic acid (20 mg) was dissolved in the reaction mixture. The resulting mixture was allowed to react overnight in the dark at room temperature and the reaction product was purified twice employing silica gel thin-layer chromatography using a chloroform:methanol (3:1) mixture as developing solvent to yield a 2-ethyl-5-aminopentanoic acid-carboxyfluorescein conjugate of the formula:

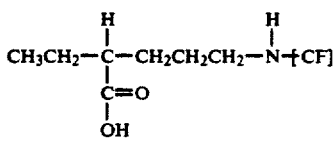

EXAMPLE VII

An active ester of carboxyfluorescein was prepared by dissolving N-hydroxysuccinimide (5 mg), carboxyfluoescein (7.5 mg) and N,N'-dicyclohexylcarbodiimide (20 mg) in 0.5 ml of pyridine. The reaction was allowed to proceed for two hours at room temperature, after which time 5-(γ-aminopropylidene)-5H-dibenzo[a,d]-10,11-dihydrocycloheptene (20 mg) was dissolved in the reaction mixture. The resulting mixture was allowed to react overnight in the dark at room temperature and the reaction product was purified twice employing silica gel thin-layer chromatography using a chloroform:methanol (3:1) mixture as developing solvent to yield a 5-(γ-aminopropylidene)-5H-dibenzo[a,d]-10,11-dihydrocycloheptene-carboxyfluorescein conjugate of the formula:

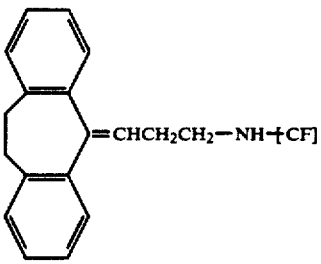

EXAMPLE VIII

A solution containing desipramine hydrochloride (1.33 g) and chloroacetyl chloride (0.8 g) in 25 ml of chloroform was refluxed for two hours. The chloroform was evaporated and the residue was dissolved in 25 ml of acetone. Sodium iodide (0.75 g) was added to the acetone solution, and the solution was refluxed for thirty minutes. The solution was filtered and the precipitated salt was rinsed with acetone. The acetone filtrate was evaporated and the residue was taken up in 20 ml of methanol. Concentrated ammonium hydroxide (20 ml) was added to the methanol solution and the resulting solution was refluxed for one hour. The reaction mixture was extracted three times with 25 ml of chloroform and combined extracts were dried over sodium sulfate, filtered and evaporated to yield N-aminoacetyldesipramine which was used without further purification.

N-aminoacetyldesipramine (5 mg) and carboxyfluorescein (5 mg) were dissolved in 0.5 ml of pyridine. To the mixture was added N,N'-diclohexylcarbodiimide (15 mg). The reaction proceeded for two hours at room temperature, after which time the reaction product was purified twice employing silica gel thin-layer chromatography using a chloroform:acetone (1:1) mixture as developing solving to yield a N-aminoacetyldesipramine-carboxyfluorescein conjugate of the formula:

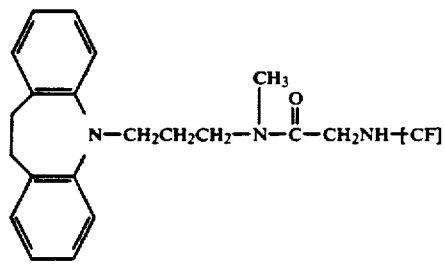

EXAMPLE IX

A solution containing N-hydroxysuccinimide (5 mg), carboxyfluorescein (7.5 mg) and N,N'-dicyclohexylcarbodiimide (20 mg) in 1 ml of pyridine was allowed to react at room temperature for four hours. An active ester of carboxyfluorescein was precipitated by adding 10 ml of diethylether to the reaction mixture. The precipitate was filtered, rinsed well with diethylether and redissolved in 0.5 ml of dimethylsulfoxide. L-thyroxine (10 mg) was then added to the solution and the reaction was allowed to proceed for two hours at room temperature after which time the reaction product was purified twice employing silica gel thin-layer chromatography using a chloroform:methanol (3:1) mixture as developing solvent to yield a L-thyroxinecarboxyfluorescein conjugate of the formula:

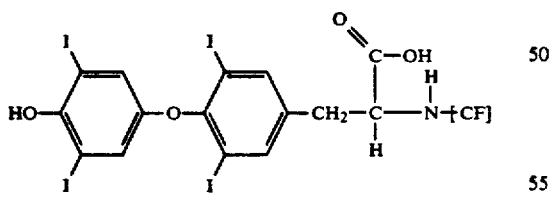

EXAMPLE X

A solution containing ammonium acetate (0.89 g), 3-oxodigoxigenin (389 mg) and sodium cyanoborohydride (63 mg) in 5 ml of methanol was stirred at room temperature for 48 hours. The solution was adjusted to pH 1 by the addition of concentrated hydrochloric acid and evaporated to dryness under reduced pressure. The residue was taken up in 10 ml of water and extracted three times with 10 ml of chloroform. The aqueous layer was adjusted to pH 11 by using solid potassium hydroxide. The resulting solution was extracted five times with 10 ml of methylene chloride. The organic layers were combined, dried and then evaporated to dryness under reduced pressure to yield 3-amino-3-deoxydigoxigenin which was used without further purification.

An active ester of carboxyfluorescein was prepared by dissolving N-hydroxysuccinimide (5 mg), carboxyfluorescein (7.5 mg) and N,N'-dicyclohexylcarbodiimide (20 mg) in 0.5 ml of pyridine. The reaction was allowed to proceed for two hours at room temperature, after which time a 3-amino-3-deoxydigoxigenin-carboxyfluorescein conjugate of the formula was isolated:

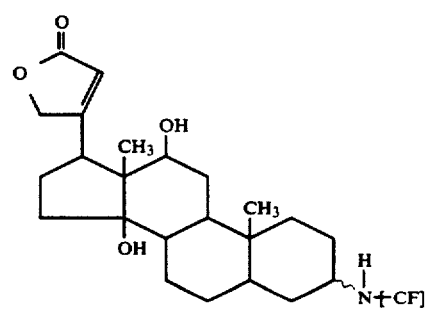

The following tracers were also prepared in accordance with the procedure previously described:

EXAMPLE XI

O-Aminoacetyl-propranolol-carboxyfluorescein conjugate

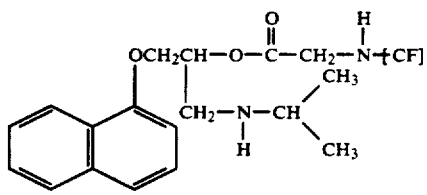

EXAMPLE XII

2-Propyl-5-aminopentanoic acid-carboxyfluorescein conjugate

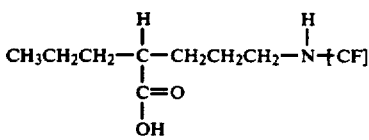

EXAMPLE XIII

2-Butyl-5-aminopentanoic acid-carboxyfluorescein conjugate

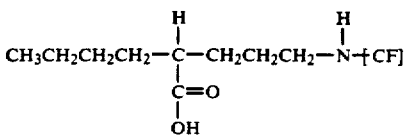

EXAMPLE XIV

Aminoprimidone-carboxyfluroescein conjugate

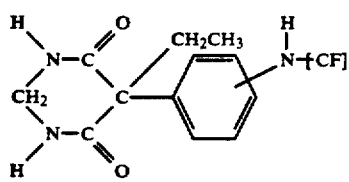

EXAMPLE XI 1-(4'-nitrophenyl)-1-hydroxy-2-amino-3-hydroxypropane-carboxyfluorescein conjugate

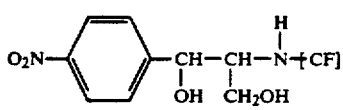

EXAMPLE XVI p-aminophenol-carboxyfluorescein conjugate

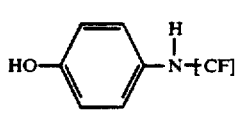

EXAMPLE XVII

N-(2-aminoethyl)-ethosuximide-carboxyfluorescein conjugate

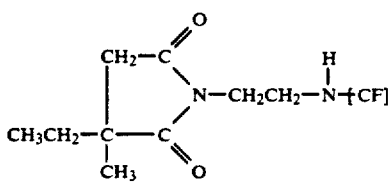

EXAMPLE XVIII

N'-desethyl-N-acetyl-procainamide-carboxyfluorescein conjugate

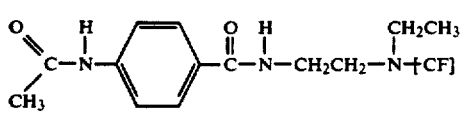

EXAMPLE XIX

N'-desethyl-N'-aminoacetyl-N-acetyl-procainamide-carboxy-fluorescein conjugate

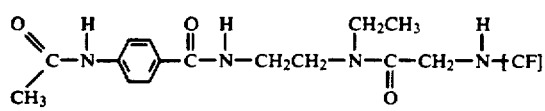

EXAMPLE XX 1-amino-2-phenyl-2-(2'-pyridyl)-4-(diisopropylamino)-butane-carboxyfluorescein conjugate

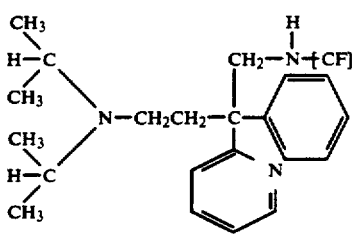

EXAMPLE XXI 3,3',5-Triiodo-L-thyronine-carboxyfluorescein conjugate

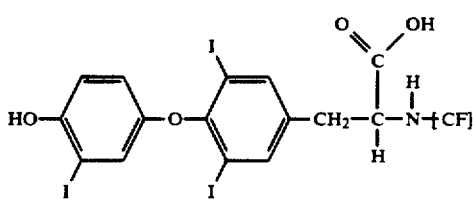

EXAMPLE XXII 3,3',5,5'-tetraiodo-D-thyronine-carboxyfluorescein conjugate

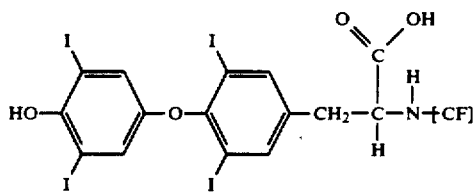

EXAMPLE XXIII

N-aminoacetyl-iminodibenzyl carboxyfluorescein conjugate

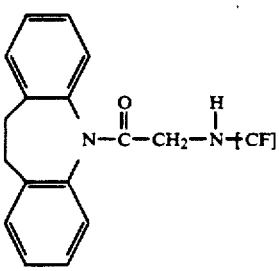

EXAMPLE XXIV

Carbhydrazinoimino-dibenzyl carboxyfluorescein conjugate

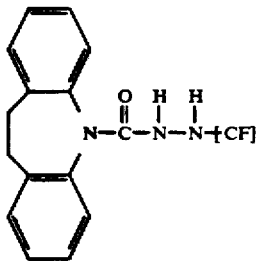

EXAMPLE XXV

Dibenzosuberonehydrazone fluorescein conjugate

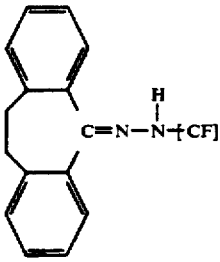

EXAMPLE XXVI 5-amino-10,11-dihydro-5H-dibenzo-[a,d]-cycloheptene

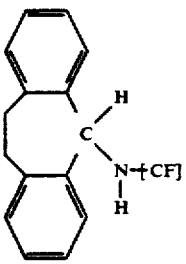

As previously mentioned, the tracers of the present invention are effective reagents for use in fluorescence polarization immunoassays. The following Examples illustrate the suitability of tracers of the present invention in immunoassays employing fluorescence polarization techniques. Such assays are conducted in accordance with the following general procedure:

(1) A measured volume of standard or test serum is delivered into a test tube and diluted with buffer;

(2) A known concentration of a tracer of the present invention optionally containing a surfactant is then added to each tube;

(3) A known concentration of antisera is added to the tubes;

(4) The reaction mixture is incubated at room temperature; and (5) The amount of tracer bound to antibody is measured by fluorescence polarization techniques as a measure of the amount of ligang in the sample.

EXAMPLE XXVII

Phenytion assay (A) Materials required:

(1) BGG buffer consisting of 0.1 M sodium phosphate, pH 7.5, containing bovine gammaglobulin, 0.01% and sodium azide, 0.01%.

(2) Tracer, consisting of 2-$\beta$-aminoethyl phenytoin-carboxyfluorescein at a concentration of approximately 105 nM in BGG buffer with 5% sodium cholate added.

(3) Antiserum, consisting of antiserum raised against phenytion diluted appropriately in BGG buffer containing 0.005% benzalkonium chloride.

(4) Samples of human serum or other biological fluid containing phenytoin.

(5) Cuvettes, 10×75 mm glass culture tubes used as cuvettes.

(6) Fluorometer capable of measuring fluorescence polarization with a precision of ±0.001 units.

(B) Assay Method:

(1) A small volume of sample (0.366 microliters) is placed in each cuvette by pipetting 15 $\mu$l of sample and diluting with 600 $\mu$l BGG buffer in a dilution vessel. Next, 15 $\mu$l of diluted sample is pipetted into the cuvette followed by 600 $\mu$l BGG buffer.

(2) Tracer is added by pipetting 40 $\mu$l tracer and 1000 $\mu$l BGG buffer into the cuvette.

(3) Antiserum is added to start the reaction by pipetting 40 $\mu$l antiserum into the cuvette followed by 1000 $\mu$l BGG buffer.

(4) The contents of all cuvettes are well mixed and allowed to incubate for 15 minutes at ambient temperature.

(5) The fluorescence polarization is read on a fluorometer and a standard curve constructed to determine unknowns.

(C) The results of a series of serum standards containing phenytoin at concentrations between 0 and 40 $\mu$g/ml are presented below. Each concentration was assayed in duplicate and averaged.

| Concentration of Phenytoin ($\mu$g/ml) | Polarization |
|---|---|
| 0 | 0.222 |
| 2.5 | 0.196 |
| 5.0 | 0.178 |
| 10.0 | 0.154 |
| 20.0 | 0.132 |
| 40.0 | 0.110 |

The polarization of fluorescence is seen to decrease in a regular manner as the phenytoin concentration increases, allowing construction of a standard curve. Unknown specimens treated in an identical manner can be quantitated by reference to the standard curve, thereby illustrating the utility of 2-$\beta$-aminoethyl phenytoin-carboxyfluorescein for the measurement of phenytoin.

EXAMPLE XXVIII

Phenobarbital assay (A) Materials required:

(1) BGG buffer (see Phenytoin)

(2) Tracer, consisting of aminophenobarbital carboxyfluorescein at a concentration of approximately 110 nM in tris HCl buffer, pH 7.5, containing 0.01% sodium azide, 0.01% bovine gamma globulin, and 0.125% sodium dodecyl sulfate.

(3) Antiserum, consiting of antiserum against phenobarbital diluted appropriately in BGG buffer containing 0.005% benzalkonium chloride.

(4) Samples of human serum or other biological fluid containing phenobarbital.

(5) Cuvettes (see Phenytoin)

(6) Fluorometer (see Phenytoin)

(B) Assay Protocol:

A small volume of sample (0.196 microliter) is placed in the cuvette by pipetting 10 μl of sample and diluting with 500 μl BGG buffer in a dilution vessel. Next, 10 μl of diluted sample is pipetted into the cuvette followed by 500 μl BGG buffer.

(2) Tracer is added by pipetting 40 μl of tracer and 1000 μl BGG buffer into each cuvette. (3) Antiserum is added to start the reaction by pipetting 40 μl antiserum followed by 1000 μl BGG buffer.

(4) The contents of all cuvettes are mixed well and allowed to incubate for 15 minutes at ambient temperature.

(5) The fluorescence polarization is read on a fluorometer and a standard curve constructed to determine unknowns.

(C) The results of a series of serum standards containing phenobarbital at concentrations between 0 and 80 μg/ml are presented below. Each concentration was assayed in duplicate and the values averaged.

| Concentration of Phenobarbital (μl) | Polarization |
|---|---|
| 0 | 0.250 |
| 5.0 | 0.231 |
| 10.0 | 0.196 |
| 20.0 | 0.150 |
| 40.0 | 0.104 |
| 80.0 | 0.077 |

The polarization of fluorescence is seen to decrease in a regular manner as the phenobarbital concentration increases, allowing construction of a standard curve. Unknown specimens treated in an identical manner can be quantitated by references to the standard curve thereby illustrating the utility of arbital-carboxyfluorescein for the measurement of phenobarbital.

EXAMPLE XXIX

Theophylline assay (A) Materials required:

(1) Tracer, consisting of 2 nM of 8-aminoethyl theophylline-carboxyfluorescein in BGG buffer (see Phentoin assay) containing 0.01% sodium dodecyl sulfate.

(2) Antiserum, consisting of antiserum raised against theophylline diluted appropriately in BGG buffer.

(3) Samples of human serum or other biological fluid containing theophylline.

(4) Cuvettes, (see Phenytoin assay)

(5) Fluorometer, (see Phenytoin assay)

(B) Assay protocol:

(1) Place 1.0 ml tracer in all cuvettes.

(2) Add 2.0 μl sample to all cuvettes.

(3) Add 1.0 ml antiserum to all cuvettes.

(4) Mix well and incubate 15 minutes at ambient temperature.

(5) Read the fluorescence polarization on a fluorometer and construct a standard curve.

(C) The results of a series of serum standards containing theophylline at concentrations between 0 and 40 μg/ml are presented. Each concentration was assayed in duplicate and the average is presented.

| Concentration of Theophylline (μg/ml) | Polarization |
|---|---|
| 0 | 0.158 |
| 2.5 | 0.118 |
| 5 | 0.105 |
| 10 | 0.091 |
| 20 | 0.076 |
| 40 | 0.063 |

The polarization of fluorescence is seen to decrease in a regular manner as the theophylline concentration increases, allowing construction of a standard curve. Unknown specimens treated in an identical manner can be quantitated by reference to the standard curbe thereby illustrating the utility of 8-aminoethyltheophylline-carboxyfluorescein for the measurement of the theophylline.

EXAMPLE XXX

Digoxin assay (A) Materials required:

(1) BGG buffer consisting of 0.1 M sodium phosphate, pH 7.5, containing bovine gammaglobulin, 0.01% and sodium azide, 0.01%.

(2) Tracer, consisting of digoxin carboxyfluorescein at a concentration of approximately 2nM in BGG buffer.

(3) Antiserum, consisting of rabbit antiserum raised against digoxin diluted appropriately in BGG buffer.

(4) Samples of human serum or other biological fluid containing phenytoin.

(5) Precipitation reagent—5% trichloroacetic acid in water.

(6) Cuvettes, 10×75 mm glass culture tubes used as cuvettes.

(7) Fluorometer capable of measuring fluorescence polarization with a precision of ±0.001 units.

(B) Assay protocol:

(1) To 100 μl of 5% trichloroacetic acid in a test tube is added 100 μl of a standard or unknown sample. The tubes containing the sample are capped and vortexed.

(2) The tubes containing standard or sample in trichloroacetic acid are centrifuged.

(3) To a test tube 1.8 ml of BGG buffer and 25 μl of antisera at 35° C. is added 150 μl of the trichloroacetic supernatant solution.

(4) The test tubes containing antisera and supernatant is incubated for 6 minutes at 35° C., at which time the fluorescence polarization of the tubes are measured. This measurement is the background fluorescence polarization of the standard or unknown.

(5) Ten minutes after the addition of supernatant to antisera, 25 μl of the tracer is added to the test tube.

(6) Six minutes after the addition of tracer, the fluorescence polarization of the standards and sample tubes are measured and the previously measured background fluorescence polarization is substracted to yield the fluorescence polarization of the antibody-tracer complex that had formed.

(7) The results of a series of serum standards containing digoxin at concentrations between 0 and 5 ng/ml are presented below. Four samples at each concentration were assayed and averaged.

| Digoxin Concentration (ng/ml) | Polarization |
|---|---|
| 0 | 0.142 |
| 0.5 | 0.134 |
| 1.0 | 0.123 |
| 2.0 | 0.106 |
| 3.0 | 0.092 |
| 5.0 | 0.070 |

The polarization of fluorescence is seen to decrease in a regular manner as the digoxin concentration increases, allowing construction of a standard curve. Unknown specimens treated in an identical manner can be quantitated by reference to the standard curve, thereby illustrating the utility of digoxin carboxyfluorescein for the measurement of digoxin.

The following table summarizes the various fluorescence polarization assays that have been carried out in accordance with the above-described procedures employing tracers prepared in the preceeding examples. The tracers employed are identical by Example number and the specific ligand(s) determined are indicated.

| Example No. | Ligand(s) |
|---|---|
| I | Phenobarbital |
| II | Phenytoin |
| III | Phenytoin |
| IV | Theophylline |
| V | Theophylline |
| VI | Valproic acid |
| VII | Nortriptyline; Amitriptyline |
| VIII | Imipramine; Desipramine |
| IX | Thyroxine |
| X | Digoxin |
| XI | Propranolol |
| XII | Valproic acid |
| XIII | Valproic acid |
| XIV | Primidone |
| XV | Chloramphenicol |
| XVI | Acetaminophen |
| XVII | Ethosuximide |
| XVIII | N-acetylprocainamide |
| XIX | N-acetylprocainamide |
| XX | Disopyramide |
| XXI | Triiodothyronine |
| XXII | Thyroxine |
| XXIII | Imipramine; Desipramine |
| XXIV | Imipramine; Desipramine |
| XXV | Nortriptyline; Amitriptyline |

-continued

| Example No. | Ligand(s) |
|---|---|
| XXVI | Nortriptyline; Amitriptyline |

As evident from the above results, the tracers of the present invention are effective reagents in fluorescence polarization immunoassays. In addition to the properties mentioned above, the tracers of the present invention possess a high degree of thermal stability, a high degree of bound polarization, high quantum yields and are realitively easy to produce and purify.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula:

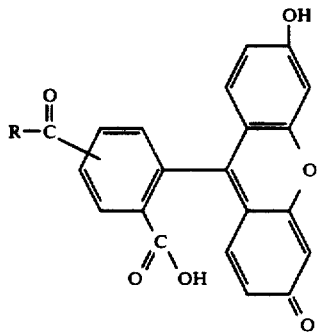

wherein R is a digoxin derivative having the formula:

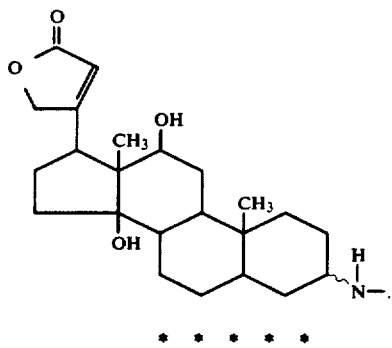

* * * * *